United States Patent [19]

Lin

[11] Patent Number: 4,809,597

[45] Date of Patent: Mar. 7, 1989

[54] CIRCULATORY SYSTEM STERILIZER

[76] Inventor: Shui T. Lin, No. 164, Chang Lu Road, Changhua City, Taiwan

[21] Appl. No.: 49,956

[22] Filed: May 15, 1987

[51] Int. Cl.[4] .............................................. A23L 1/00
[52] U.S. Cl. .................................... 99/483; 99/323.3; 99/470
[58] Field of Search ................. 99/359, 355, 470, 389, 99/483, 276, 516, 534, 536, 366, 403, 471, 468, 467, 367, 323.3; 426/524, 511, 418, 521, 520, 407, 412; 422/25, 26, 297, 302, 295, 292

[56] References Cited

U.S. PATENT DOCUMENTS

| | | | |
|---|---|---|---|
| 4,003,302 | 1/1977 | Mencacci et al. | 99/359 |
| 4,073,226 | 2/1978 | Shulz | 99/443 C |
| 4,082,510 | 4/1978 | Jovanovic | 99/483 X |
| 4,085,668 | 4/1978 | Mughannam | 99/483 |
| 4,102,256 | 7/1978 | John et al. | 99/359 X |
| 4,179,986 | 12/1979 | Mencacci | 426/232 |
| 4,667,590 | 5/1987 | Balaam et al. | 99/470 |

Primary Examiner—Timothy F. Simone
Attorney, Agent, or Firm—Browdy & Neimark

[57] ABSTRACT

A circulatory steam sterilizer and, in particular, the circulatory steam sterilizer having a steam boiler poised in a transverse array and its two ends respectively joined with two-tier compartment partition plates which are arranged in an asymmetrical manner in a plurality of layers and the inner compartment partition plates are connected and in communication with the transversely arranged conduits. The conduits in the upper-most conduits for discharge and delivery are connected and communicative to the outer compartment partition plates, and then these inner conduits are transversely arranged in the inner part of the conduits in the lower layer to specially generate the inner and outer double circulatory heating, thereby achieving the multi-purpose practical benefits live circulatory preheating, heated sterilization and cooling as its features.

8 Claims, 2 Drawing Sheets

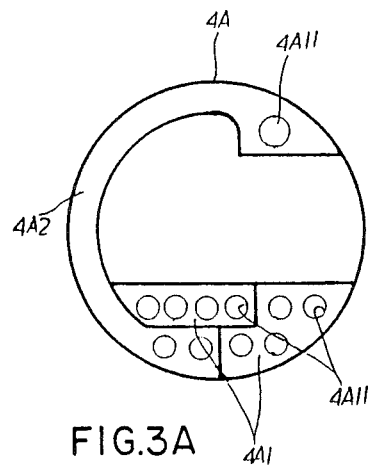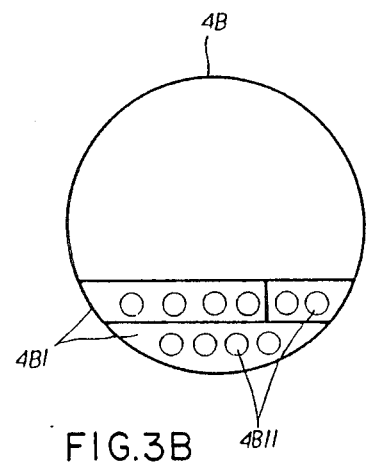
FIG.3A  FIG.3B
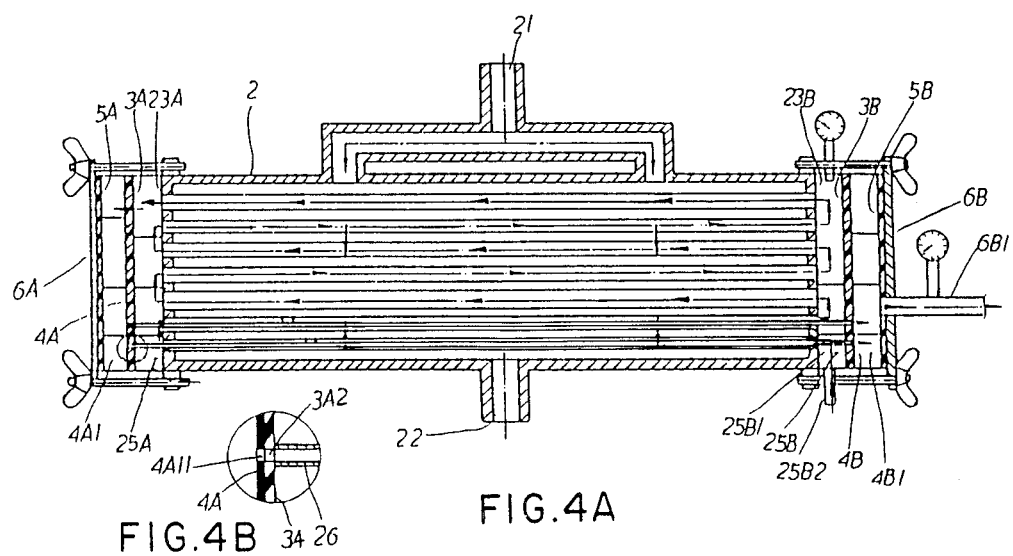
FIG.4A  FIG.4B

CIRCULATORY SYSTEM STERILIZER

BACKGROUND OF THE INVENTION

1. Field of the Invention

The present invention relates to a "circulatory steam sterilizer" involving the innovative design of a sterilizer for liquid circulatory heating purposes, and, in particular, a steam boiler in a transversely-laid rack form that has conduits transversely arranged in its inner part, and the two ends of said boiler are respectively joined with the inner compartment partition plates in an opposite but asymmetrical arrangement, and then said inner compartment partition plates are joined to connect and communicate the outer compartment plates by the conduits in the upper-most layer and are also guided to the lower layer, where the inner conduits are transversely arranged in the inner side of above said conduits to generate the upward circulatory heating, and then the abovesaid conduits are guided to the lower layer for the heat exchange by performing the preheating and the cooling processes at the same time.

2. The Prior Art

Since the pre-packing sterilization treatment is an integral process for the beverage manufacturing sector, the common operators often employ the high temperature treatment by means of steam boilers. However, as to the manufacture and use of steam boilers, the main point lies in that the circulation of the liquid conduits in the steam boilers must be good in order to increase the process of the inlet liquid flow so as to cut the space cost of the volume of the equipment and also to maximize the sterilization effects. But in the old type liquid conduits, only their body is made for circulation and when these conduits are connected to the inner part of the boiler, the procedures required to form continuous pipelines are often quite complicated. Further too many welded points are needed on the bent portions of the pipe body, so the excellent effects of precision, accuracy and durability of the conduits are often seldom seen. Additionally, it is also usually extremely difficult to clean or wash them, since extraneous objects maybe deposited at, thereby clogging the bends of the conduits so that they do not conform to sanitation requirements. In this way the manufacture and maintenance cost is relatively increased. Therefore evidently it is quite worth our consideration on their practicability to trade such a higher cost off the lower benefits in their use.

SUMMARY OF THE INVENTION

The primary object of the present invention is that in direct response to the defects of the circulatory system of conventional steam boilers which often has high manufacture costs and low efficiency, all the said disadvantages are eliminated, and a circulatory steam sterilizer is provided and particularly a transversely laid steam boiler provided with a plurality of conduits which are separately sealed inside, but the openings on both ends of each of said conduits are open and communicative to the compartments formed by the compartment partition plates which are joined to the two ends of said steam boiler. The areas of the respective opposite compartments of said compartment partition plates are of a half number of them in symmetrical arrangement, and the lower end outlet of their inlet is provided on the upper end to produce upward circulatory communicative force. The steam inlet is provided on the center of the upper end of the sterilizer, while the steam outlet is provided on the bottom of the sterilizer to make the liquid produce the upwardly gradual preheating and heating circulation for the high temperature sterilization as its feature.

The next object of the present invention is to provide a circulatory steam sterilizer having double circulatory preheating and heating to reach the highly efficient heat exchange for a high temperature sterilization and in particular the sterilizer, wherein the outer end of the inner compartment partition plates are connected to the outer compartment partition plates and also the conduit outlets are made communicative to the compartments of the outer compartment partition plates, the compartment are also of a half number of them in a symmetrical arrangement. In the lower section of said compartments, the inner conduits are provided in the afore-said conduits in a mutually communicative manner to lead the liquids, which have gone through the high temperature sterilization in said conduits, to the inner conduits, thereby conducting the inner and outer preheating on the liquid in the conduits in the lower section and also cooling off the liquid in the conduits at the same time.

A further object of the present invention is to provide a circulatory steam sterilizer having the dialysis, separation and washing and cleaning convenience to meet the sanitary requirements. One of its features lies in that the outer compartment partition plates for dialysis and separation, and the conduits and inner conduits are arranged in a straight line form without any bends, while the inner conduits are extractable and separable, and particularly provide simple easy maintenance and cleaning operations.

BRIEF DESCRIPTION OF THE DRAWING

Now, in conjunction with drawings, the contents of the present invention and the functions and benefits it can achieve are detailed as follows:

FIGS. 3A and 3B are views showing the arrangement of opposite compartments of the outer compartment partition plates.

FIGS. 4A and 4B are views showing the action of the fluid in cross section along the line IV—IV of FIG. 1 according to the present invention.

DETAILED DESCRIPTION OF THE PREFERRED EMBODIMENT

Figure 1:
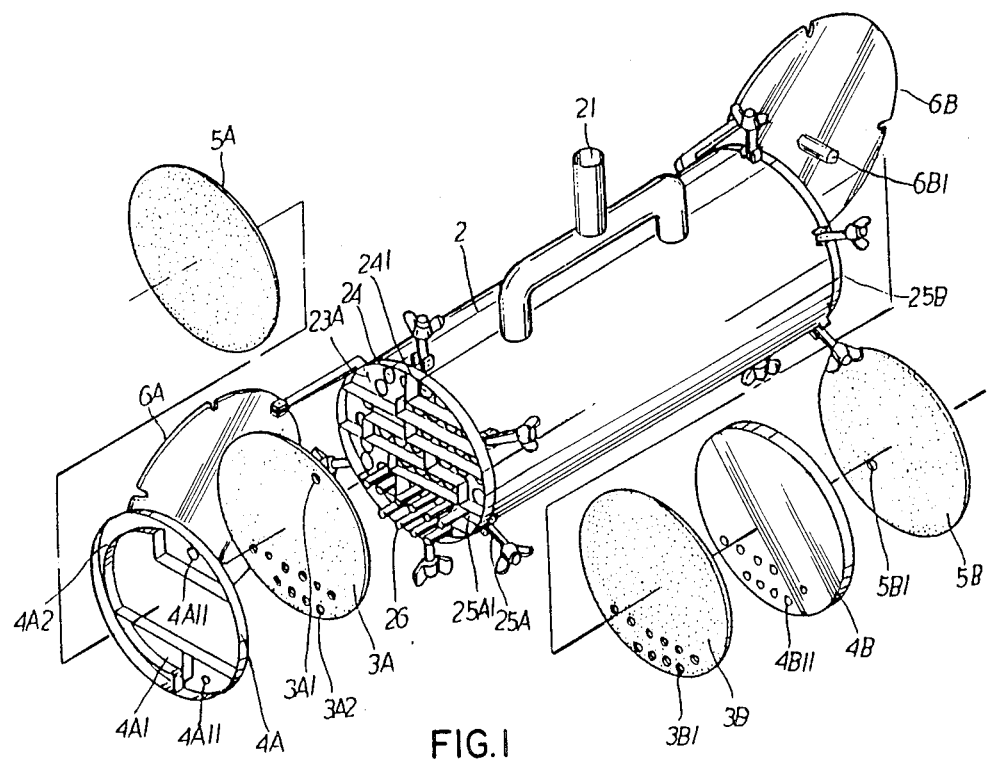
FIG. 1 is a partial three-dimensional exploded view according to the present invention.
Figure 2A:
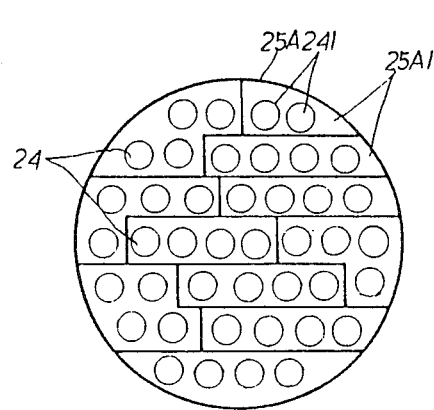
FIGS. 2A and 2B are views showing the arrangement of opposite compartments of the inner compartment partition plates.
Figure 2B:
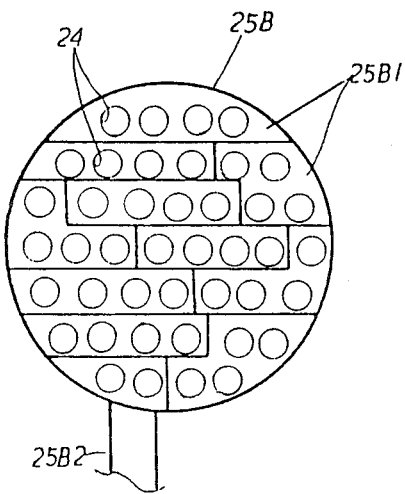

Firstly, referring to the circulatory steam sterilizer in FIG. 1 mainly composed of a transverse cylindrical steam boiler, the two ends of which are combined by the leak-proof washers 3A, 3B, and 5A, 5B and the outer compartment partition plates 4A, 4B, which mesh the movable covers 6A, 6B, in an interlocking form. The steam boiler 2 is laid in a transverse cylindrical position. A steam inlet 21 is provided on the top of said boiler 2 and a steam outlet 22 is provided on the bottom of said boiler 2 for the steam entry and discharge respectively. A plurality of communicative conduits 24 are transversely arranged in the inner part of said boiler, and the end faces 23A, 23B on both sides of said boiler support and secure said conduits to form a multi-layer arrangement. The openings at the ends of said conduits 24 are distributed on the end faces 23A, 23B. The compartment partition plates 25A, 25B having a plurality of compartments 25A1, 25B1 are provided in a protruding form on the periphery of the end faces 23A, 23B. However of the areas of said compartments 25A1, 25B1 are mutually opposite (please see FIG. 2) to make the two ends of the same conduit 24 open out into different compartments, to make various other conduits mutually communicative, and also to make the discharge part 241 of said conduits 24 open into the upper section compartment 25A1 on the inner compartment partition plate 25A. The liquid inlet 25B2 is provided on the lower end of the lower section compartment 25B1 of the inner compartment partition plate 25B. The inner conduits 26 are provided in the lower section compartment and bolted transversely inside the conduits 24 to form an inner and outer double-layer conduit.

The leak-proof washers 3 are made, in coordination with the configuration of the inner compartment plate 25A, into a round shape, of which, one leak-proof washer 3A is located adjacent to the discharge port 241 of conduit 24 and is with a through hole 3A1. Further, a plurality of through holes 3A2, 3B1 are symmetrically arranged at the opposite positions on the lower sections of said two washers 3A, 3B and may choke off the communication of the end opening of the inner conduit 26.

The outer compartment partition plate 4 is like the shape of the inner compartment partition plate 25, and a compartment 4A1 is formed at the position of the discharge part 241 of the corresponding conduit on the upper section of the outer compartment partition plate 4A and is also provided with a through-hole 4A11 which is communicative with the through-hole 3A1 on the leak-proof washer 3A. A plurality of compartments 4A1 each having at least one through-hole 4A11 are provided on the lower section to communicate the conduits 26 with one another and further a conduit channel 4A2 passes between the upper and lower compartments. Another outer compartment partition plate 4B is provided with a plurality of compartments 4B1 to form a partial area communication with the compartments 4A1 (please see FIG. 3), thereby making the liquid discharged from the discharge port 241 of the conduit 24 enter the inner part of the outer compartment partition plate 4, so the area formed by the compartments 4A1, 4B1 and inner conduits 26 limits the conduit flow to achieve the circulatory flow.

The leakage-proof washers 5A, 5B are pasted on the surface of the outer compartment partition plate 4 to make various compartments form air/water tight compartments which in turn make the liquid conduct circulatory flow according to the guiding of compartments. The washer 5B is provided with a through-hole 5B1 to make the liquid therein guided and discharged therefrom.

The afore-said leakage-proof washers 3A, 3B, and the leakage-proof washers 5A, 5B of the outer compartment plates 4A, 4B entirely depend on the covers 6A, 6B which are pivoted on the two ends the steam boiler to connect and fix the inner compartment partition plates 25A, 25B in the two ends of said steam boiler and they are locked by bolts. A discharge pipe 6B1 is provided on the cover 6B and is disposed just opposite to the through-hole 5B1 in the leakage-proof washer 5B to cause the circulatory liquid to be discharged therefrom.

Referring to FIG. 4 since the steam inlet 21 is provided on the upper side of said steam boiler 2, and the outlet 22 is provided on the lower side of said steam boiler 2. A plurality of liquid conduits 24 are transversely arranged in the inner part of said boiler in a separate laminated array to make the openings on the two ends of said conduit 24 provided on the end faces 23A, 23B and also communicative to the compartments 25A1, 25B1 of the inner compartment partition plates 25A, 25B. Further the compartments 25A1, 25B1 of the compartment partition plates are in the form of their partial area symmetry such that the two ends of said conduit 24 are connected and communicative respectively to a different compartment concerned. Meanwhile the compartments are closed and stopped by the leakage-proof washers 3A, 3B to make the conduit 24 and compartments 25A1, 25B1 mutually communicative, thereby forming a continuous communicative pipeline. Further the liquid inlet 25B2 is provided in the lower section compartment of the inner compartment partition plate 25B. The discharge port 241 of the conduit is provided on the upper section compartment of the inner compartment partition plate 24A, According to the assembly of the above-said structures, the liquid can enter the lower section compartment of the inner compartment 25B from the liquid inlet 25B2 and then enter the inner part of the lower section of conduits 24, and then is guided to the lower section compartment of the inner compartment partition plate 25A and then turns to the inner part of another conduit in an upward circulatory flow in sequence and finally enters the upper section compartment of the inner compartment partition plate 25A into the conduit discharge port 241. Therefore when the steam enters the inner part of the steam boiler 2 from the inlet 21 on the upper section to form a high temperature layer, and the lower section belongs to the low temperature layer (the upper section gradually transmits and releases the heat to the conduits to make the temperature of the steam lowered when the steam reaches the lower section), and when the liquid temperature in the conduits 24 in the lower section circulates upward to reach the upper section after the steam is heated many times in the passage to obtain the maximum temperature, the effects of high temperature circulatory heating and sterilization are therefore attained.

Heated by the high temperature circulatory process, the liquid is discharged from the conduit discharge port 241 and enters into the inner side of the upper section compartment 25A1 of the inner compartment partition plate 25A. Further in coordination with the combination of the outer compartment partition plates 4A, 4B and inner conduits 26, the liquid is channelled to the inner part of the upper section compartment of the outer compartment partition plate 4A and then is guided by the conduit channel 4A2 to the lower section compartment (in conjunction with that shown in FIG. 3) and enters the inner part of the inner conduits 26, and now the liquid in the inner conduits 26 is under a high temperature state, while the liquid in the conduits 24 (on the outer part of inner conduits 26) is under a low temperature to make the liquid in the conduits 24 subject to the heat released by the liquid in the inner conduits 26 for heating and preheating (the above paragraph has described that the liquid in the conduits 24 absorbs the steam heat to produce the heating and preheating effects) and relatively to reduce the temperature of the liquid in the inner conduits 26. Henceforth the liquid in the lower section conduits 24 is subjected to inner and outer double heating and preheating, thereby to achieve the purpose of completing the preheating and cooling at the same time and is then discharged by the discharge pipe 6B1 of the cover 6B.

I claim:

1. A circulatory steam sterilizer for circulatory heated sterilization of common liquid beverages using steam, comprising:

a steam boiler for guiding the steam entering an inner part of said boiler and discharging the steam therefrom, said boiler comprising a plurality of transversely arranged outer conduits each having two open ends, arranged in a plurality of layers and supported at both ends by two end faces of said steam boiler;

a first and second inner compartment partition plates respectively secured and connected to the two end faces of said steam boiler, said second inner compartment partition plate comprising a liquid inlet;

a first and second outer compartment partition plates;

two leakage-proof washers for sealing off and connecting each of the outer compartment partition plates and the inner compartment partition plates, each of said washer including at least one through-hole for communicating the outer compartment partition plates and the inner compartment partition plates;

a first and second cover each pivotally connected to a respective end of said steam boiler to pivotally rotate, thereby pressing the outer compartment partition plates and the leakage-proof washers, said covers being lockable by bolts for proper positioning and including cover packings disposed between said covers and the respective outer compartment partition plates to avoid any seepage, said second cover including a liquid discharge pipe;

a plurality of inner conduits which are transversely bolted inside certain ones of said plurality of outer conduits in a lower section of said boiler for making the two ends of said boiler directly urge against said leakage-proof washers and communicative to the outer compartment partition plates, and wherein the combination of the above-listed elements causes the liquid beverage to enter the liquid inlet, and in conjunction with the conduits and the inner compartment partition plates, flow in a zig zag way through said steam boiler for circulatory flow and drainage, thereby achieving and completing preheating, heating and cooling processes.

2. The circulatory steam sterilizer in claim 1, wherein the steam inlet of said steam boiler is provided at an upper section of said steam boiler and the discharge port is provided at a lower section of said boiler.

3. The circulatory steam sterilizer in claim 1, wherein the open ends of the conduits are communicative to the end faces of said steam boiler and to areas outside said steam boiler.

4. The circulatory steam sterilizer in claim 1, wherein said inner compartment partition plates comprise means for forming a plurality of compartments in an asymmetrical upside-down mirror image arrangement such that the ends of certain conduits communicate with different compartments which in turn makes a continuous conduit between the compartments and the conduits.

5. The circulatory steam sterilizer in claim 4, wherein the compartment in the first inner compartmer partition plate that is connected to an end of a flow-path formed by said conduits is located at an upper position on the first inner compartment partition plate.

6. The circulatory steam sterilizer in claim 5, wherein a compartment on an upper section of said first outer compartment partition plate is opposite to the compartment at the upper section of said first inner compartment partition plate and said compartment on the first outer compartment partition plate comprises a through-hole for communicating with said compartment at the upper section of said first inner compartment partition plate;

a plurality of compartments are provided on a lower section of said first inner compartment partition plate and a through-hole is provided on said first inner compartment partition plate to communicate ends of the inner conduits; and a conduit channel is provided between an upper one of said compartments and a lower one of said compartments for channeling and mutual communication.

7. The circulatory steam sterilizer of claim 1, wherein a plurality of compartments are provided on a lower section of the second outer compartment partition plate and in an asymmetrical position-parity arrangement with respect to the compartments provided on the lower section of the first outer compartment partition plate, said second outer compartment partition plate including a through-hole for communicating with an inner conduit, thereby making the inner conduit and the compartments mutually mesh together to form an inner circulatory flow-path.

8. The circulatory steam sterilizer in claim 1, wherein said plurality of conduits have an inner diameter larger than an outer diameter of said inner conduits.

* * * * *